(12) United States Patent
Schabbach et al.

(10) Patent No.: US 10,143,801 B2
(45) Date of Patent: Dec. 4, 2018

(54) DRIVE MECHANISM FOR A NEEDLE INSERTION ARRANGEMENT

(71) Applicant: Sanofi-Aventis Deutschland GMBH, Frankfurt am Main (DE)

(72) Inventors: Michael Schabbach, Frankfurt am Main (DE); Meinolf Werner, Worms (DE); Olaf Zeckai, Weinheim (DE); Philippe Nzike, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 292 days.

(21) Appl. No.: 14/916,669

(22) PCT Filed: Sep. 2, 2014

(86) PCT No.: PCT/EP2014/068598
§ 371 (c)(1),
(2) Date: Mar. 4, 2016

(87) PCT Pub. No.: WO2015/032744
PCT Pub. Date: Mar. 12, 2015

(65) Prior Publication Data
US 2016/0279330 A1    Sep. 29, 2016

(30) Foreign Application Priority Data
Sep. 5, 2013   (EP) .................................... 13183153

(51) Int. Cl.
*A61M 5/20* (2006.01)
*A61M 5/32* (2006.01)
*A61M 5/46* (2006.01)

(52) U.S. Cl.
CPC ............ *A61M 5/20* (2013.01); *A61M 5/3287* (2013.01); *A61M 5/46* (2013.01); *A61M 2005/206* (2013.01)

(58) Field of Classification Search
CPC .................. A61M 5/3287; A61M 5/20; A61M 2005/206; A61M 37/0084; A61M 37/0076; D05B 55/04; D05B 55/02; D05B 55/16; D05B 55/14; D05B 55/06; D05B 55/00
See application file for complete search history.

(56) References Cited

U.S. PATENT DOCUMENTS

| 4,658,744 A * | 4/1987 | Takauchi ............... D05B 69/24 112/448 |
| 2008/0269687 A1* | 10/2008 | Chong .................... A61L 15/58 604/180 |

FOREIGN PATENT DOCUMENTS

| CN | 103128025 | 6/2013 |
| DE | 202009003050 | 8/2010 |

OTHER PUBLICATIONS

Translation of CN 103128025; translation from Google Patents; accessed Feb. 28, 2018.*

(Continued)

*Primary Examiner* — Laura Bouchelle
*Assistant Examiner* — Tasnim M Ahmed
(74) *Attorney, Agent, or Firm* — Fish & Richardson P.C.

(57) ABSTRACT

The invention relates to a drive mechanism for a needle insertion arrangement, the drive mechanism comprising: an actuator, a rotatable drive pulley directly or indirectly coupled to the actuator, and a belt adapted to engage the drive pulley and adapted to be fixed to a needle retainer.

16 Claims, 4 Drawing Sheets

Specification includes a Sequence Listing.

(56) References Cited

OTHER PUBLICATIONS

International Search Report and Written Opinion in International Application No. PCT/EP2014/068598, dated Sep. 24, 2014, 8 pages.
International Preliminary Report on Patentability in International Application No. PCT/EP2014/068598, dated Mar. 8, 2016, 6 pages.

* cited by examiner

SEQUENCE LISTING

<160> NUMBER OF SEQ ID NOS: 1

<210> SEQ ID NO 1
<211> LENGTH: 39
<212> TYPE: PRT
<213> ORGANISM: Artificial Sequence
<220> FEATURE:
<223> OTHER INFORMATION: Exendin-4(1-39), insulin analogue or derivative

<400> SEQUENCE: 1

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

DRIVE MECHANISM FOR A NEEDLE INSERTION ARRANGEMENT

CROSS-REFERENCE TO RELATED APPLICATIONS

This application is a U.S. national stage application under 35 USC § 371 of International Application No. PCT/EP2014/068598, filed on Sep. 2, 2014, which claims priority to European Patent Application No. 13183153.9, filed on Sep. 5, 2013, the entire contents of which are incorporated herein by reference.

TECHNICAL FIELD

The invention relates to a drive mechanism for a needle insertion arrangement.

BACKGROUND OF THE INVENTION

Administering an injection is a process which presents a number of risks and challenges for users and healthcare professionals, both mental and physical. During manual insertion of an injection needle into an injection site, e.g. the skin of a patient, it may be difficult to avoid tilting and bending of the needle and the insertion may be slow thus causing pain.

There remains a need for an improved drive mechanism for a needle insertion arrangement.

SUMMARY OF THE INVENTION

Aspects of the present invention can provide an improved drive mechanism for a needle insertion arrangement The aspects can be implemented by a drive mechanism for a needle insertion arrangement according to claim 1.

Exemplary embodiments of the invention are given in the dependent claims.

According to the invention a drive mechanism for a needle insertion arrangement comprises
 an actuator,
 a rotatable drive pulley directly or indirectly coupled to the actuator, and
 a belt adapted to engage the drive pulley and adapted to be fixed to a needle retainer.

In an exemplary embodiment the drive mechanism comprises a needle retainer adapted to retain an injection needle, the needle retainer arranged to be moved between a retracted position and an extended position.

In an exemplary embodiment the actuator is arranged as an electrical motor.

In an exemplary embodiment a gear is arranged for coupling the actuator to the drive pulley.

In an exemplary embodiment the gear is arranged as a spur-geared drive.

In an exemplary embodiment the gear comprises a first gear wheel coupled to the actuator, and a second gear wheel engaging the first gear wheel, wherein the drive pulley is coupled to the second gear wheel.

In an exemplary embodiment the drive mechanism further comprises two deflection pulleys, wherein the belt is guided over the deflection pulleys, wherein the belt is fixed to the needle retainer between the two deflection pulleys.

In an exemplary embodiment the retracted position and/or the extended position are/is defined by the needle retainer abutting one of the deflection pulleys.

In an exemplary embodiment the belt is arranged as an O-belt, a V-belt, a poly-V-belt, a flat belt or a toothed belt.

The drive mechanism may be applied in an insertion arrangement for moving an injection needle between a retracted position and an extended position, comprising a disposable unit, comprising a needle base, to which the needle is fixed, and the drive mechanism, wherein the needle retainer is adapted to retain the needle base.

The insertion arrangement has only limited space requirements thus allowing for low profile injection devices with a high wearing comfort. The insertion arrangement achieves high speed needle movements and exact needle guidance thus reducing pain for the patients when inserting and retracting the needle and increasing consumer acceptance and satisfaction. The low part count of the insertion arrangement and the low requirements for electronic equipment allow for an increased mechanical robustness and low manufacturing costs. The insertion arrangement is a fault-tolerant system. The movement of the needle may be customized to the respective application by modifying a gear transmission ratio of the gear, e.g. by respectively selecting the sizes of the first gear wheel, the second gear wheel and the drive pulley. Application of a gear reduces the torque to be provided by the actuator. In an exemplary embodiment the actuator may be replaced by a handle for manually operating the drive mechanism.

Further scope of applicability of the present invention will become apparent from the detailed description given hereinafter. However, it should be understood that the detailed description and specific examples, while indicating exemplary embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
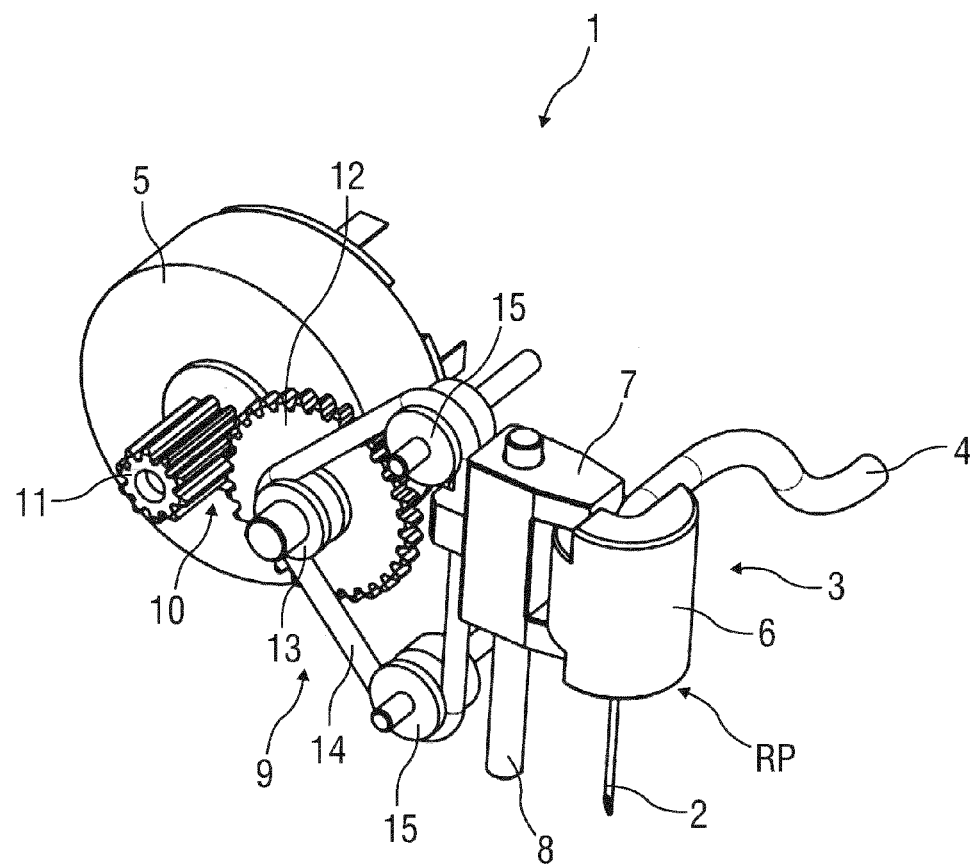
FIG. 1 is a schematic perspective view of an exemplary embodiment of an insertion arrangement for inserting and/or retracting an injection needle.

FIG. 1 is a schematic perspective view of an exemplary embodiment of an insertion arrangement 1 for automatically or semi-automatically inserting an injection needle 2 into an injection site. The arrangement 1 may be applied in medicament pumps, e.g. insulin pumps which may be permanently worn on the body.

The injection needle 2 is part of a disposable unit 3, further comprising a tube 4 for establishing a fluid communication of the needle 2 with a drug container (not illustrated) and comprising a needle base 6, to which the injection needle 2 may be fixed for mechanically connecting the needle 2 to a drive mechanism 9 of an injection unit (not illustrated). The needle base 6 is inserted in a forked needle retainer 7 which is arranged to be moved up and down in a linear guide 8. This linear movement corresponds to insertion of the needle 2 into the injection site, e.g. subcutaneous body tissue and removal from the injection site, respectively.

The drive mechanism 9 for the needle 2 comprises an actuator 5, e.g. an electrical motor, coupled to a belt 14 through a gear 10. The gear 10 may be arranged as a spur-geared drive comprising a first gear wheel 11 directly coupled to the actuator 5, and a second gear wheel 12 engaging the first gear wheel 11. A drive pulley 13 is directly coupled to the second gear wheel 12 and adapted to engage the belt 14 which is guided over two deflection pulleys 15. Between the two deflection pulleys 15 the belt 14 is fixed to the needle retainer 7. If the actuator 5 is rotated, the rotation is forwarded through the gear 10 to the belt 14 which conveys the needle retainer 7 and the needle 2 along the linear guide 8. Depending on a rotational direction of the actuator 5 the needle retainer 7 is moved towards a retracted position RP or towards an extended position (best seen in FIG. 4).

The belt 14 may be arranged as an O-belt, a V-belt, a poly-V-belt, a flat belt or a toothed belt.

Figure 2:
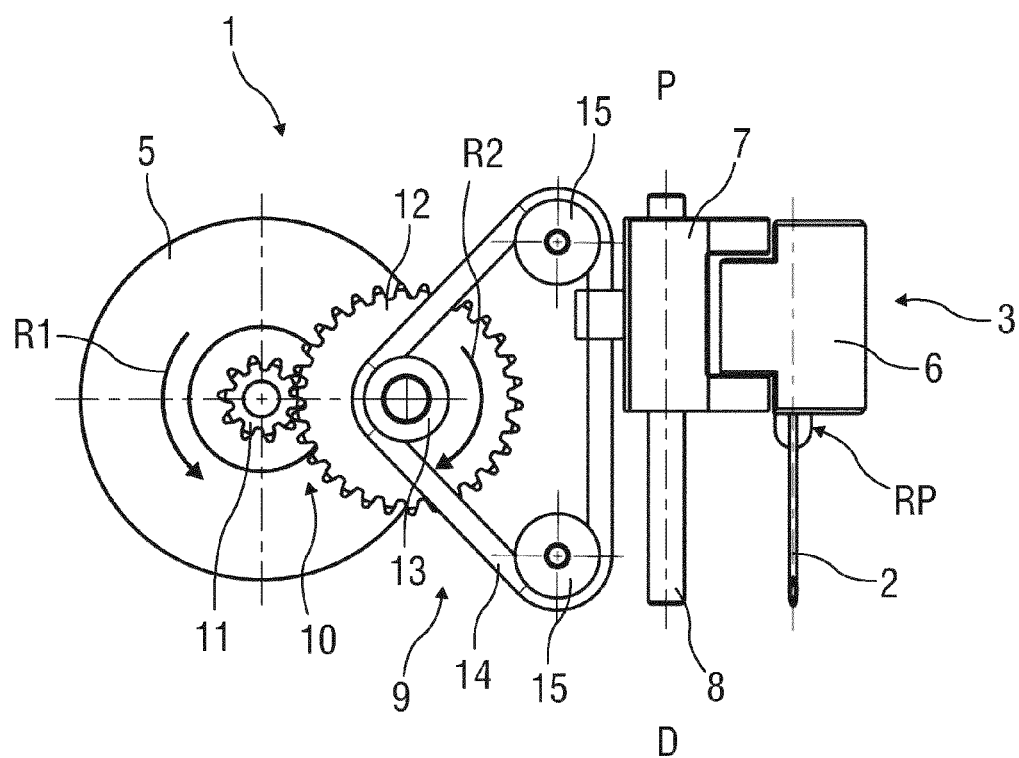
FIG. 2 is a schematic side view of the insertion arrangement in an initial position with the needle in a retracted position.

A sequence of operation of the insertion arrangement 1 is as follows:

FIG. 2 is a schematic side view of the insertion arrangement 1 in an initial position. The disposable unit 3 with the needle base 6, the needle 2 and the tube 4 has been inserted in the forked needle retainer 7. The needle retainer 7 and the needle 2 are in the retracted position RP. The actuator 5 starts rotating in a first rotational direction R1. The rotation is forwarded through the gear 10 so that the drive pulley 13 is rotated in a second rotational direction R2 opposed to the first rotational direction R1. The belt 14 coupled to the drive pulley 13 is thus conveyed and moves the needle retainer 7 with the needle 2 in a distal direction D.

Figure 3:
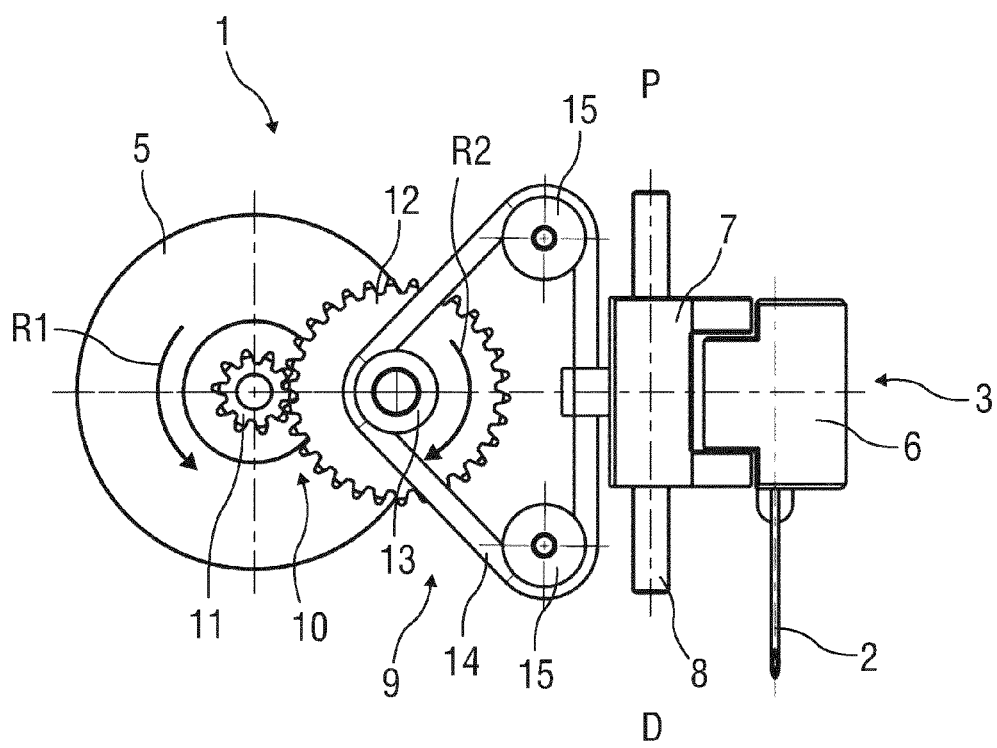
FIG. 3 is a schematic side view of the insertion arrangement during movement of the needle retainer in the distal direction.

FIG. 3 is a schematic side view of the insertion arrangement 1 during movement of the needle retainer 7 in the distal direction D. The actuator 5 and the gear 10 have reached their nominal rotation speeds thus moving the needle retainer 7 and the needle 2 in the distal direction D at a high speed.

Figure 4:
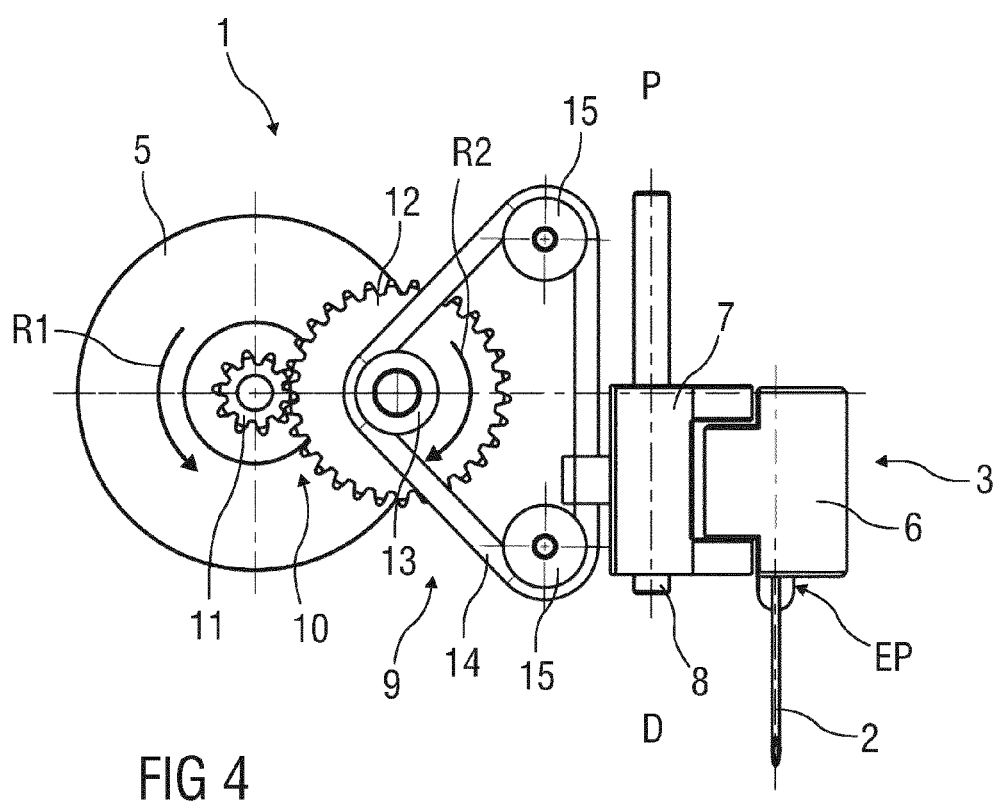
FIG. 4 is a schematic side view of the insertion arrangement with the needle in an extended position.

FIG. 4 is a schematic side view of the insertion arrangement 1 with the needle retainer 7 and the needle 2 having reached an extended position EP. A needle insertion depth, e.g. in the subcutaneous body tissue, may be determined by the needle retainer 7 abutting a stop (not illustrated) on the linear guide 8 or by the needle retainer 7 abutting one of the deflection pulleys 15. The actuator 5 and the gear 10 have come to a standstill.

The needle 2 may subsequently retracted in an analogous manner by rotating the actuator in the second rotational direction R2 thereby also reversing the rotation of the drive pulley 13 and moving the needle retainer 7 and the needle 2 in a proximal direction P towards the retracted position RP as in FIG. 2.

The movement of the needle 2 may be customized to the respective application by modifying a gear transmission ratio of the gear, e.g. by respectively selecting the sizes of the first gear wheel 11, the second gear wheel 12 and the drive pulley 13. Thus, the drive mechanism 9 may be modified to perform fast or slow movements of the needle retainer 7. Fast movements of the needle retainer 7 and the needle 2 into the retracted position RP and the extended position are facilitated by the elasticity of the belt 14 and possible transmission-slip between the drive pulley 13 and the belt 14. For example, the speed of the movements may be specified to mimic a typical manual needle insertion or retraction.

In an alternative embodiment the actuator 5 may be directly coupled to the drive pulley 13 without an intermediate gear 10.

In an alternative embodiment the actuator 5 may be arranged as a spring motor or as a handle for manually operating the drive mechanism 9.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

LIST OF REFERENCES 1 insertion arrangement
2 injection needle
3 disposable unit
4 tube
5 actuator
6 needle base
7 needle retainer
8 linear guide
9 drive mechanism
10 gear
11 first gear wheel
12 second gear wheel
13 drive pulley
14 belt
15 deflection pulley
R1 first rotational direction
R2 second rotational direction

The invention claimed is:

1. Drive mechanism for a needle insertion arrangement of an injection device, the drive mechanism comprising:
   an actuator;
   a rotatable drive pulley directly or indirectly coupled to the actuator;
   a belt adapted to engage the drive pulley and adapted to be fixed to a needle retainer arranged to be moved up and down in a linear guide; and
   two deflection pulleys, wherein the belt is guided over the deflection pulleys, wherein the belt is fixed to the needle retainer between the two deflection pulleys.

2. Drive mechanism according to claim 1, comprising the needle retainer adapted to retain an injection needle, the needle retainer arranged to be moved between a retracted position (RP) and an extended position (EP).

3. Drive mechanism according to claim 2, wherein the retracted position (RP) or the extended position (EP) is defined by the needle retainer abutting one of the deflection pulleys.

4. Drive mechanism according to claim 1, wherein the actuator comprises an electrical motor.

5. Drive mechanism according to claim 1, wherein a gear is arranged for coupling the actuator to the drive pulley.

6. Drive mechanism according to claim 5, wherein the gear comprises a spur-geared drive.

7. Drive mechanism according to claim 6, wherein the gear comprises a first gear wheel coupled to the actuator, and a second gear wheel engaging the first gear wheel, wherein the drive pulley is coupled to the second gear wheel.

8. Drive mechanism according to claim 1, wherein the belt comprises at least one of an O-belt, a V-belt, a poly-V-belt, a flat belt or a toothed belt.

9. Insertion arrangement for moving an injection needle between a retracted position (RP) and an extended position (EP), the insertion arrangement comprising:
   a disposable unit comprising a needle base to which the needle is fixed; and
   a drive mechanism comprising:
      an actuator;
      a rotatable drive pulley directly or indirectly coupled to the actuator;
      a belt adapted to engage the drive pulley and adapted to be fixed to a needle retainer arranged to be moved up and down in a linear guide, wherein the needle retainer is adapted to retain the needle base; and
      two deflection pulleys, wherein the belt is guided over the deflection pulleys, wherein the belt is fixed to the needle retainer between the two deflection pulleys.

10. The insertion arrangement according to claim 9, comprising the needle retainer, the needle retainer arranged to be moved between a retracted position (RP) and an extended position (EP).

11. The insertion arrangement according to claim 10, wherein the retracted position (RP) or the extended position (EP) is defined by the needle retainer abutting one of the deflection pulleys.

12. The insertion arrangement according to claim 9, wherein the actuator comprises an electrical motor.

13. The insertion arrangement according to claim 9, wherein a gear is arranged for coupling the actuator to the drive pulley.

14. The insertion arrangement according to claim 13, wherein the gear comprises a spur-geared drive.

15. The insertion arrangement according to claim 14, wherein the gear comprises a first gear wheel coupled to the actuator, and a second gear wheel engaging the first gear wheel, wherein the drive pulley is coupled to the second gear wheel.

16. An auto-injector comprising:
   insertion arrangement for moving an injection needle between a retracted position (RP) and an extended position (EP), the insertion arrangement comprising:
      a disposable unit comprising a needle base to which the needle is fixed; and
      a drive mechanism comprising:
         an actuator;
         a rotatable drive pulley directly or indirectly coupled to the actuator;
         a belt adapted to engage the drive pulley and adapted to be fixed to a needle retainer arranged to be moved up and down in a linear guide, wherein the needle retainer is adapter to retain the needle base; and
         two deflection pulleys, wherein the belt is guided over the deflection pulleys, wherein the belt is fixed to the needle retainer between the two deflection pulleys; and
   a drug container coupled to the injection needle, the drug container carrying a medicament consisting of at least one pharmaceutically active compound.

* * * * *

UNITED STATES PATENT AND TRADEMARK OFFICE
CERTIFICATE OF CORRECTION

PATENT NO. : 10,143,801 B2
APPLICATION NO. : 14/916669
DATED : December 4, 2018
INVENTOR(S) : Michael Schabbach et al.

Page 1 of 1

It is certified that error appears in the above-identified patent and that said Letters Patent is hereby corrected as shown below:

In the Claims

Column 10, Line 37, Claim 16, delete "adapter" and insert -- adapted --

Signed and Sealed this
Twenty-eighth Day of January, 2020

Andrei Iancu
*Director of the United States Patent and Trademark Office*